United States Patent
Howley et al.

(10) Patent No.: US 7,300,658 B2
(45) Date of Patent: Nov. 27, 2007

(54) RECOMBINANT POXVIRUS COMPRISING AT LEAST TWO COMPOX ATI PROMOTERS

(75) Inventors: Paul Howley, Glen Waverly (AU); Sonja Leyrer, München (DE)

(73) Assignee: Bavarian Nordic A/S, Kvistgaard (DK)

( * ) Notice: Subject to any disclaimer, the term of this patent is extended or adjusted under 35 U.S.C. 154(b) by 0 days.

(21) Appl. No.: 10/535,371

(22) PCT Filed: Nov. 12, 2003

(86) PCT No.: PCT/EP03/12610

§ 371 (c)(1), (2), (4) Date: May 4, 2005

(87) PCT Pub. No.: WO2004/048582

PCT Pub. Date: Jun. 10, 2004

(65) Prior Publication Data

US 2006/0153874 A1   Jul. 13, 2006

(30) Foreign Application Priority Data

Nov. 25, 2002 (DK) .............................. 2002 01814

(51) Int. Cl.
*A61K 39/275* (2006.01)
*A61K 39/12* (2006.01)
*C12Q 1/70* (2006.01)
*C12Q 1/68* (2006.01)
*C12P 19/34* (2006.01)

(52) U.S. Cl. .............................. 424/232.1; 424/186.1; 435/5; 435/6; 435/91.1; 435/91.33

(58) Field of Classification Search .................... None
See application file for complete search history.

(56) References Cited

U.S. PATENT DOCUMENTS 5,443,964 A * 8/1995 Pickup et al. .............. 435/69.1

FOREIGN PATENT DOCUMENTS

| WO | WO 97/02355 | 1/1997 |
| WO | WO 02/18585 | 3/2002 |

OTHER PUBLICATIONS

Blanchard et al. Modified vaccinia virus Ankara undergoes limited replication in human cells and lacks several immunomodulatory proteins: implications for use as a human vaccine, Journal of General Virology, 1998, vol. 79, pp. 1159-1167.*
A Vaccinia Virus Transfer Vector . . . by M. Howley et al. (Gen2, 172 (1996).
Conserved Taaat Motif in Vaccinia Virus . . . by M. Hänggi et al. (FMBO Journal, 1986).
High-Level Expression of Amsacta Moorei . . . by Y. Ki et al. (Journal of Gen. Virology 1998).

* cited by examiner

*Primary Examiner*—Bruce R. Campell
*Assistant Examiner*—Sharon Hurt
(74) *Attorney, Agent, or Firm*—Jonathan Myers; Andrew Wilford

(57) ABSTRACT

Recombinant poxvirus are disclosed comprising in the viral genome at least two expression cassettes, each comprising a cowpox ATI promoter according to SEQ ID NO:1, a polynucleotide sequence in which not more than 6 nucleotides are substituted, deleted, and/or inserted into SEQ ID NO:1 and still active as an ATI promoter, or a polynucleotide comprising at least 10 nucleotides including nucleotides 22 to 29 of SEQ ID NO: 1 and still active as an ATI promoter and a coding sequence, wherein the expression of the coding sequence is regulated by said promoter or said polynucleotides. The recombinant poxviruses are useful as pharmaceutically active ingredients in the preparation of vaccines.

21 Claims, 3 Drawing Sheets

SEQUENCE LISTING

```
<160> NUMBER OF SEQ ID NOS: 1

<210> SEQ ID NO 1
<211> LENGTH: 29
<212> TYPE: DNA
<213> ORGANISM: Cowpox virus
<220> FEATURE:
<221> NAME/KEY: promoter
<222> LOCATION: (1)..(29)

<400> SEQUENCE: 1
gttttgaata aaattttttt ataataaat                                  29
```

RECOMBINANT POXVIRUS COMPRISING AT LEAST TWO COMPOX ATI PROMOTERS

CROSS REFERENCE TO RELATED APPLICATIONS

Figure 1:
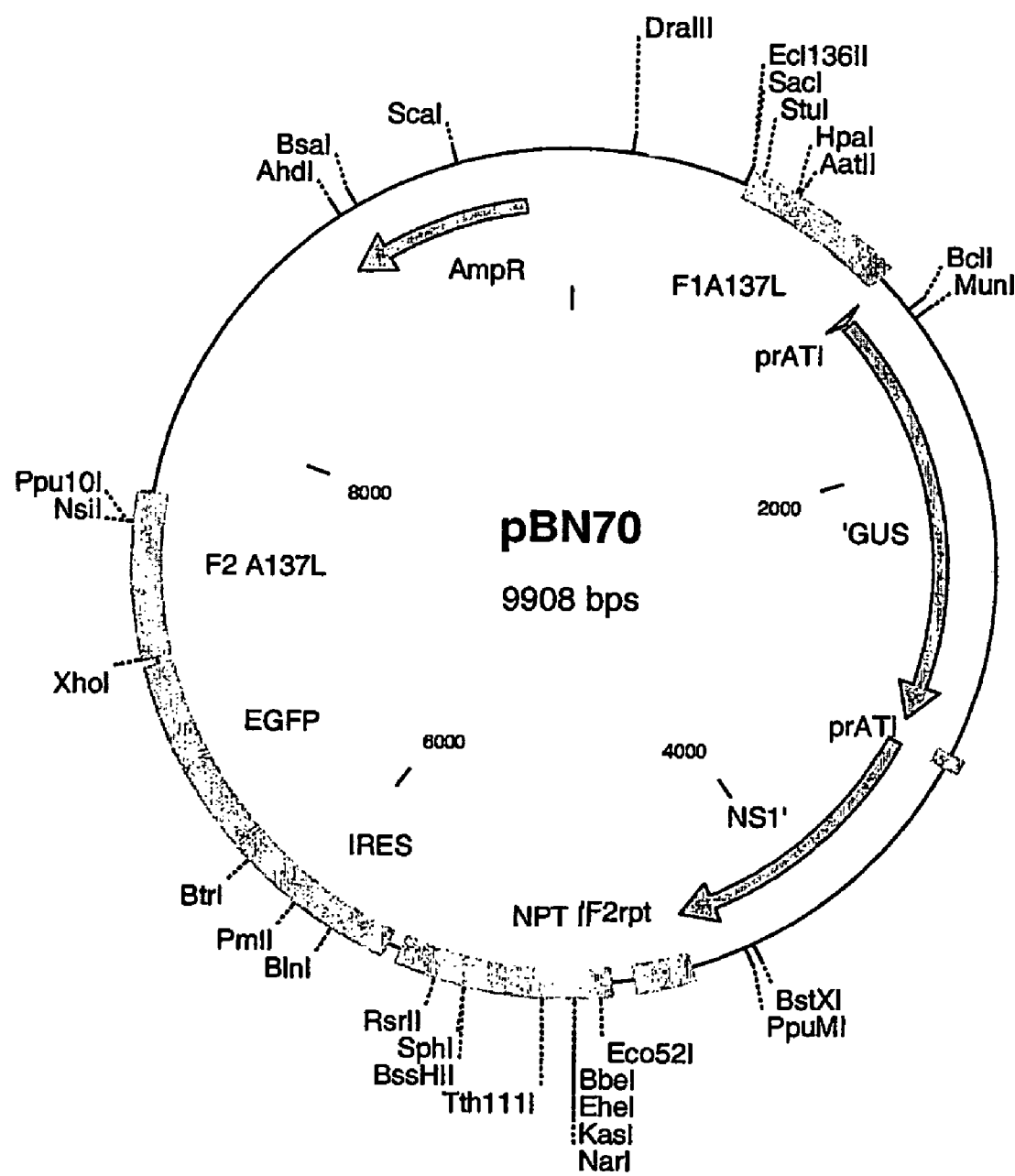

This application is the U.S. national phase of PCT application PCT/EP2003/012610, filed 12 Nov. 2003, published 10 Jun. 2004 as WO 2004/048582 A2, and claiming the priority of Danish Patent Application PA 2002 01814 filed 25 Nov. 2002.

This investigation was done in order to prove that a recombinant virus based on the MVA-BN vector technology is stable although two cowpox ATI promoters are inserted at two different intergenic regions (IGRs) of MVA-BN (see WO02/42480). Therefore we were generating a virus carrying two HIV genes (termed "HIV1" and "HIV2") in two different IGRs, namely IGR 44/45 at position 37,000 and IGR I4L/I5L at position 56,700. Both genes were driven by the same ATI promoter sequence. The virus was plaque purified and tested after more than 20 passages.

To demonstrate the stability of our construct we were amplifying the regions next to the two insertions (~5 kb in length) and the regions spanning the inserted genes (~5.5 kb in length). The reactions were carried out with the recombinant virus (recMVA) and the wild type MVA-BN as control. The obtained eight PCR fragments were digested with restriction enzymes to get a specific restriction pattern. The fragments were analyzed on a 1% agarose gel. With the help of the restriction pattern it should be possible to make occurring instabilities visible, as deletions or insertions would change the restriction pattern. The size of the expected fragments for the wild type virus (MVA-BN) and the recombinant MVA-BN (recMVA) are shown below the enclosed figure.

Our results show, that the two PCRs of the surrounding area show the same pattern for the recMVA as for the wild type MVA-BN indicating that these regions are stable although they have genes inserted next to it. The two PCRs spanning the regions with the insertions show small differences between MVA-BN and the recMVA, which account for the inserted genes. For HIV-1 of the recMVA-BN there is an additional 628 bp band next to the 637 bp band, the latter being visible in both, MVA-BN and recMVA. Moreover, a 128 bp band is missing in the recMVA-BN. For HIV-2 MVA-BN has an additional 877 bp band and recMVA-BN has two additional bands, one at 565 and one at 354 which are next to 355, the latter being visible in both, recMVA and MVA-BN. Thus, the pattern of all four PCRs for wild type and recombinant virus match exactly with the predicted fragment sizes leading to the conclusion that our recombinant virus is stable. The experiments have not given any hint that the recombinant MVA comprising two ATI promoters in the genome might be instable or show a tendency towards homologous recombination between the ATI promoter sequences.

OBJECT OF THE INVENTION

It was the object of the present invention to provide stable recombinant poxviruses harboring at least two expression cassettes, preferably for genes that are not naturally part of the poxviral genome, wherein it should be possible to produce the proteins encoded by said at least two different expression cassettes in similar amounts.

DETAILED DESCRIPTION OF THE INVENTION

This object has been solved by the provision of recombinant poxviruses comprising in the viral genome at least two expression cassettes, each comprising the cowpox ATI promoter or a derivative thereof and a coding sequence, wherein the expression of the coding sequence is regulated by said promoter or derivative thereof.

It was shown by the present inventors that poxviruses comprising two or more copies of the ATI promoter are unexpectedly stably; it was demonstrated that no detectable recombination events occurred between the homologous or even identical ATI promoter sequences. This is in contrast to vaccinia viruses comprising two or more p7.5 promoters in the viral genome.

According to the present invention the poxvirus may be any poxvirus in which the expression of genes should be regulated by the ATI promoter or derivative thereof. Thus, the poxvirus may be any virus of the subfamily of Chordopoxvirinae and Entomopoxvirinae (see Fields Virology $3^{rd}$ edition, Lippincott-Raven Publishers, Philadelphia, USA, Chapter: 83, ISBN 0-7817-0253-4). Viruses from the subfamily Chordopoxvirinae are particularly preferred if the recombinant poxvirus is used to express genes in mammalian animals, including humans. Particularly preferred genera belonging to the subfamily Chordopoxvirinae are Orthopoxviruses, Parapoxviruses, Avipoxviruses, Capripoxviruses, Leporipoxviruses and Suipoxviruses. Most preferred are Orthopoxviruses and Avipoxviruses. Examples for avipoxviruses are canarypoxviruses and fowlpoxviruses. An example for an Orthopoxvirus is vaccinia virus. The vaccinia virus strain that may be used according to the present invention may be any vaccinia virus strain, such as strains Copenhagen, Temple of Heaven, Wyeth, Western Reserve, Elstree, NYCBH and so on. Particularly preferred is Modified Vaccinia Ankara (MVA). MVA has been generated by 516 serial passages on chicken embryo fibroblasts of the Ankara strain of vaccinia virus (CVA) (for review see Mayr, A., et al., Infection 3, 6-14 [1975]). As a consequence of these long-term passages the resulting MVA virus deleted about 31 kilobases of its genomic sequence and, therefore, was described as highly host cell restricted to avian cells (Meyer, H. et al., J. Gen. Virol. 72, 1031-1038 [1991]). It was shown, in a variety of animal models that the resulting MVA was significantly avirulent (Mayr, A. & Danner, K. [1978] Dev. Biol. Stand. 41: 225-34). Additionally, this MVA strain has been tested in clinical trials as vaccine to immunize against the human smallpox disease (Mayr et al., Zbl. Bakt. Hyg. I, Abt. Org. B 167, 375-390 [1987], Sticki et al., Dtsch. med. Wschr. 99, 2386-2392 [1974]).

According to the present invention any MVA strain may be used. Examples for MVA virus strains used according to the present invention and deposited in compliance with the requirements of the Budapest Treaty are strains MVA 572 and MVA 575 deposited at the European Collection of Animal Cell Cultures (ECACC), Salisbury (UK) with the deposition numbers ECACC V94012707 and ECACC V00120707, respectively and MVA-BN with the deposition number ECACC V00083008.

The most preferred MVA-strain is MVA-BN or a derivative thereof. The features of MVA-BN, the description of biological assays allowing to evaluate whether a MVA strain is MVA-BN or a derivative thereof and methods allowing to obtain MVA-BN or a derivative thereof are disclosed in WO 02/42480. The content of this application is included in the present application by reference.

In general terms it is preferred to use viruses that are not harmful for the animal including a human, if the virus is used to vaccinate or to treat the animal including a human. For humans particularly safe poxviruses are the different vaccinia virus strains, such as MVA and avipoxviruses such as fowlpoxvirus and canarypoxvirus.

In order to propagate poxviruses, eukaryotic cells are infected with the virus. The eukaryotic cells are cells that are susceptible to infection with the respective poxvirus and allow replication and production of infectious virus. Such cells are known to the person skilled in the art for every poxvirus species. For MVA an example for this type of cells are chicken embryo fibroblasts (CEF) and BHK cells (Drexler I., Heller K., Wahren B., Erfle V. and Sutter G., J. Gen. Virol. (1998), 79, 347-352). CEF cells can be cultivated under conditions known to the person skilled in the art. Preferably the CEF cells are cultivated in serum-free medium in stationary flasks or roller bottles. The incubation preferably takes place 48 to 96 hours at 37° C.±2° C. For the infection MVA is preferably used at a multiplicity of infection (MOI) of 0.05 to 1 $TCID_{50}$ and the incubation preferably takes place 48 to 72 hours at 37° C.±2° C.

The sequence of the promoter of the cowpox virus A-type inclusion protein gene (ATI promoter) is known to the person skilled in the art. In this context reference is made to the Genebank entry accession number D00319. A preferred ATI promoter sequence is shown as SEQ ID.: No. 1 and is as follows:

5' GTTTT GAATA AAATT TTTTT ATAAT AA<u>AT</u> 3'

According to the present invention it is possible to use the ATI promoter as specified in SEQ. ID.:No. 1 or to use a derivative of the ATI promoter, which may be a subsequence of the sequence according to SEQ. ID.:No. 1. The term "subsequence of the sequence according to SEQ. ID.:No. 1" refers to shorter fragments of the sequence of SEQ. ID.:No. 1 that are still active as a promoter, in particular as vaccinia virus late promoter. A typical fragment of the sequence of SEQ. ID.:No. 1 has a length of at least 10 nucleotides, more preferably of at least 15 nucleotides, even more preferably of at least 20 nucleotides, most preferably of at least 25 nucleotides of the sequence of SEQ. ID.:No. 1. The subsequence preferably may comprise nucleotides 25 to 29 of SEQ. ID.:No. 1, i.e. the sequence 5'-TAAAT-3' located at the 3' end of SEQ. ID.:No. 1. The subsequence may also comprise nucleotides 22 to 29 of SEQ. ID.:No. 1, i.e. the sequence 5'-TAATAAAT3' located at the 3' end of SEQ. ID.:No. 1.

The promoter may be inserted upstream of a coding sequence in such a way that nucleotides 28 to 29 of SEQ. ID: 1 (underlined in the sequence above) are part of the 5' ATG 3' start codon of translation. Alternatively, the promoter may be separated by several nucleotides from the start codon of translation. The spacer between the 3' end of the promoter according to SEQ. ID.: No 1 and the A in the 5' ATG 3' start codon is preferably less than 100 nucleotides, more preferably less than 50 nucleotides and even more preferably less than 25 nucleotides. However, the spacer might even be longer as long as the promoter is still capable of directing the expression of the coding sequence located downstream of the promoter.

The derivative of the ATI promoter can also be a sequence that has one or more nucleotide substitutions, deletions and/or insertions with respect to the sequence of SEQ ID.: No. 1 or subsequences thereof, wherein said derivatives are still active as a promoter, in particular as vaccinia virus late promoter. A sequence having one or more nucleotide substitutions is a sequence in which one or more nucleotides of the sequence according to SEQ ID.: No. 1 are substituted by different nucleotides. A sequence having one or more nucleotide insertions is a sequence in which one or more nucleotides are inserted at one or more locations of the sequence according to SEQ ID.: No. 1. A sequence having one or more nucleotide deletions is a sequence in which one or more nucleotides of the sequence according to SEQ ID.: No. 1 are deleted at one or more locations. In the derivatives of SEQ ID.: No. 1 deletions, substitutions and insertions may be combined in one sequence.

Preferably the derivative has a homology of at least 40%, more preferably of at least 60%, even more preferably of at least 80%, most preferably of at least 90% when compared to the sequence of SEQ ID.: No.1. According to the most preferred embodiment not more than 6 nucleotides, even more preferably not more than 3 nucleotides are substituted, deleted and/or inserted in the sequence of SEQ ID: No. 1.

In particular, it might be preferable to keep nucleotides 25 to 29 of SEQ. ID.:No. 1, i.e. the sequence 5'-TAAAT-3' in the promoter to attain maximal promoter activity. It might also be preferable to keep nucleotides 22 to 29 of SEQ. ID.:No. 1, i.e. the sequence 5'-TAATAAAT-3 in the promoter.

The above comments regarding the location of the ATI promoter or subsequences thereof also apply to the above-defined sequences having one or more nucleotide substitutions, deletions and/or insertions with respect to the sequence according to SEQ ID.: No. 1 or with respect to subsequences thereof.

A bundle of prior art documents allows the person skilled in the art to predict which derivatives of SEQ ID.: No. 1 still have the biological activity of being active as a poxvirus virus promoter, in particular as a vaccinia virus late promoter. In this context reference is made to Chakrarbarti et al., Biotechniques (1997) 23, 1094-1097 and Davison and Moss, J. Mol. Biol. (1989) 210, 771-784. Moreover, whether a fragment is still active as a poxvirus promoter, in particular a vaccinia virus late promoter can easily be checked by a person skilled in the art. In particular the sequence derivative can be cloned upstream of a reporter gene in a plasmid construct. Said construct may be transfected into a eukaryotic cell or cell line, such as CEF or BHK cells that has been infected with a poxvirus. The poxvirus used for infection is preferably a poxvirus from the same genus and even more preferably the same poxvirus than the poxvirus in the genome of which the promoter should be inserted. The expression of the reporter gene is then determined and compared to the expression of the reporter gene controlled by the promoter according to SEQ ID.: No. 1. A derivative according to the present invention is preferably a derivative having a promoter activity in said test system of at least 10%, preferably at least 30%, more preferably at least 50%, even more preferably at least 70%, most preferably at 90% compared to the activity of the promoter sequence of SEQ ID.: No.1. Also those derivatives of SEQ ID.: No.1 are within the scope of the present invention that have a higher promoter activity than SEQ ID.: No. 1.

According to the present invention the recombinant poxvirus comprises at least two expression cassettes, each comprising an ATI promoter or a derivative thereof. In other words the genome of the recombinant poxvirus may comprise two or more ATI promoters or derivatives thereof. The ATI promoters in the viral genome may be the same or different. Thus, it may be that all of the ATI promoters have the sequence according to SEQ ID.: NO. 1. It may also be that all of the ATI promoters are the same derivative of the sequence according to SEQ ID.: No.1. Alternatively, one or more of the ATI promoters may have the sequence of SEQ ID.: NO. 1 and one or more of the ATI promoters in the same poxviral genome may be derivatives of the sequence according to SEQ ID.: NO. 1. If such a poxviral genome comprises two or more derivatives of the ATI promoter, these derivatives may be the same or different. According to a further alternative all of the ATI promoters in the poxviral genome may be different derivatives of the sequence according to SEQ ID.: NO.1.

In general terms the invention relates to recombinant poxviruses comprising at least two ATI promoters or derivatives thereof in the poxviral genome. Thus, the viral genome may comprise e.g. two, three, four, five, six or more ATI promoters or derivatives thereof in the viral genome.

The ATI promoters or derivatives thereof are usually part of expression cassettes, each comprising a cowpox ATI promoter or derivative thereof and a coding sequence, the expression of which is regulated by said promoters. The coding sequences may be any sequences the expression of which should be controlled by the ATI promoter or derivative thereof.

According to one alternative at least one of the ATI promoters in the poxviral genome may be used to express a gene that is already part of the poxviral genome. Such a gene may be a gene that is naturally part of the viral genome or a foreign gene that has already been inserted into the poxviral genome. In these cases the ATI promoter is inserted upstream of the gene in the poxviral genome, the expression of which is to be controlled by the ATI promoter.

Alternatively or additionally at least one of the ATI promoters or derivatives thereof may be part of an expression cassette that is introduced into the poxviral genome. The expression cassettes comprising an ATI promoter or derivative thereof and a coding sequence may be inserted into any suitable location of the viral genome. Without being bound to the following examples, suitable insertion sites may be selected from: (i) non-essential genes such as the TK-gene, (ii) genes that are necessary for the replication of the virus if the function of said gene is supplemented by the cell that is used for the propagation of the virus; (iii) intergenic regions of the poxviral genome, wherein the term "intergenic region" refers preferably to those parts of the viral genome located between two adjacent genes that do not comprise coding sequences; (iv) naturally occurring deletion sites of the poxviral genome. An example of a virus genome having a naturally occurring deletion site is the genome of MVA, in which certain regions are deleted with respect to the genome of the vaccinia virus strain Copenhagen.

As indicated above, the insertion sites are not restricted to these preferred insertion sites since it is within the scope of the present invention that the expression cassette may be inserted anywhere in the viral genome as long as it is possible to obtain recombinants that can be amplified and propagated in at least one cell culture system, such as Chicken Embryo Fibroblasts (CEF cells) in the case of MVA and other poxviruses such as vaccinia viruses in general and avipoxviruses.

The different expression cassettes/ATI promoters or derivatives thereof may be inserted into different insertion sites in the poxviral genome.

For various reasons it might be preferable to insert two or more expression cassettes into the same insertion site of the poxvirus genome. However, in such a case it has to be excluded that homologous recombination occurs between the different expression cassettes. Homologous recombination would lead to recombinant viruses in which parts of the expression cassettes are deleted. Since no significant parts of the poxviral vector genome are deleted the resulting recombinants are still viable. Thus, there is no selection for viruses having maintained two or more expression cassettes in the same insertion site. To avoid such undesired recombination events it was state of the art to use different promoters if two or more expression cassettes are inserted into the same insertion site. According to the present invention it is now possible to insert two or more expression cassettes, each comprising an ATI promoter or derivative thereof into the same insertion site since no homologous recombination occurs between the promoters in the expression cassettes.

Thus, according to a preferred embodiment at least two, if not all of the expression cassettes are inserted into the same insertion site in the poxviral genome. In this case the different expression cassettes are directly adjacent with no poxviral sequences between the different expression cassettes or at least with only rather short poxviral sequences between the different expression cassettes.

The methods necessary to construct recombinant poxvirus are known to the person skilled in the art. By way of example, the expression cassette and/or the ATI promoter or derivative thereof may be inserted into the poxviral genome by homologous recombination. To this end a nucleic acid is transfected into a permissive cell line, wherein the nucleic acid comprises the expression cassette and/or the ATI promoter or derivative thereof flanked by nucleotide stretches that are homologous to the region of the poxviral genome in which the expression cassette and/or the ATI promoter or derivative thereof is to be inserted. For MVA permissive cells are CEF cells and BHK cells. The cells are infected with the poxvirus and in the infected cells homologous recombination occurs between the nucleic acid and the viral genome. Alternatively it is also possible to first infect the cells with the poxvirus and then to transfect the nucleic acid into the infected cells. Again recombination occurs in the cells. The recombinant poxvirus is then selected by methods known in the prior art. The construction of recombinant poxviruses is not restricted to this particular method. Instead, any suitable method known to the person skilled in the art may be used to this end.

The ATI promoter in the recombinant poxvirus may be used to control the expression of any coding sequence(s). The coding sequence may preferably code for at least one antigenic epitope or antigen. In this case the recombinant poxvirus may be used to express said antigen after infection of cells in an organism, e.g. a mammalian animal including a human. The presentation of said antigen/epitope may elicit an immune response in the organism that may lead to a vaccination of the organism against the agent from which the antigen/epitope is derived. More specifically the epitope/antigen may by part of a larger amino acid sequence such as a polyepitope, peptide or protein. Examples for such polyepitopes, peptides or proteins may be polyepitopes, peptides or proteins derived from (i) viruses, such as HIV, HTLV, Herpesvirus, Denguevirus, Poliovirus, measles virus, mumps virus, rubella virus, Hepatitis viruses and so on, (ii) bacteria, (iii) fungi.

The proteins, peptides or epitopes expressed from the different expression cassettes may be derived from the same agent, such as a virus, bacteria or fungus. By way of example all products expressed from the expression cassettes may be HIV proteins. If all products are derived from the same agent it is possible to induce a very broad immune response against said agent. Alternatively it is also possible that the proteins, peptides or epitopes expressed from the different expression cassettes are derived from different agents. By way of example, the products derived from the expression cassettes in one poxviral genome are derived from different viruses, such as mumps, measles and rubella virus. According to this embodiment it is possible to use one recombinant poxvirus to induce an immune response against several agents.

Alternatively, at least one of the coding sequences may encode a therapeutic compound such as interleukins, interferons, ribozymes, enzymes and so one.

The recombinant poxvirus according to the present invention may be administered to the animal or human body according to the knowledge of the person skilled in the art. Thus, the recombinant poxvirus according to the present invention may be useful as a medicament (i.e. pharmaceutical composition) or vaccine.

The pharmaceutical composition or the vaccine may generally include one or more pharmaceutical acceptable and/or approved carriers, additives, antibiotics, preservatives, adjuvants, diluents and/or stabilizers in addition to the recombinant poxvirus. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycollic acids, polymeric amino acids, amino acid copolymers, lipid aggregates, or the like.

For the preparation of pharmaceutical compositions or vaccines, the recombinant poxvirus is converted into a physiologically acceptable form. This can be done based on the experience in the preparation of poxvirus vaccines used for vaccination against smallpox (as described by Stickl, H. et al., [1974] Dtsch. med. Wschr. 99, 2386-2392). For example, if the poxvirus is MVA the purified virus may be stored at $-80°$ C. with a titre of $5\times10^8$ TCID$_{50}$/ml formulated in about 10 mM Tris, 140 mM NaCl pH 7.4. For the preparation of vaccine shots, e.g., $10^1$-$10^9$ particles of the recombinant virus according to the present invention are lyophilized in phosphate-buffered saline (PBS) in the presence of 2% peptone and 1% human albumin in an ampoule, preferably a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other additives such as antioxidants or inert gas, stabilizers or recombinant proteins (e.g. human serum albumin) suitable for in vivo administration. An typical formulation suitable for freeze-drying of recombinant MVA comprises 10 mM Tris-buffer, 140 mM NaCl, 18.9 g/l Dextran (MW 36.000-40.000), 45 g/l Sucrose, 0.108 g/l L-glutamic acid mono potassium salt monohydrate pH 7.4. The glass ampoule is then sealed and can be stored between $4°$ C. and room temperature for several months. However, as long as no need exists the ampoule is stored preferably at temperatures below $-20°$ C.

For vaccination or therapy the lyophilisate can be dissolved in 0.1 to 0.5 ml of an aqueous solution, preferably water, physiological saline or Tris buffer, and administered either systemically or locally, i.e. by parenteral, intramuscular or any other path of administration know to the skilled practitioner. The mode of administration, the dose and the number of administrations can be optimized by those skilled in the art in a known manner.

Thus, according to a related embodiment the invention relates to a method for affecting, preferably inducing an immunological response in a living animal body including a human comprising administering the virus, the composition or the vaccine according to the present invention to the animal or human to be treated. If the recombinant poxvirus is a recombinant MVA a vaccine shot typically comprises at least $10^2$, preferably at least $10^4$, more preferably at least $10^6$, even more preferably $10^8$ to $10^9$ TCID$_{50}$ (tissue culture infectious dose) of the virus.

The invention further concerns a method for introducing at least two coding sequences into target cells comprising the infection of the target cells with the virus according to the present invention. The target cell may be a cell in which the virus is able to replicate or a cell that can be infected by the recombinant virus, in which the virus, however, does not replicate, such as all types of human cells in the case of recombinant MVA.

The invention further relates to a method for producing a peptide, protein and/or virus comprising the infection of a host cell with a recombinant virus according to the present invention, followed by the cultivation of the infected host cell under suitable conditions, and further followed by the isolation and/or enrichment of the peptide and/or protein and/or viruses produced by said host cell. If it is intended to produce, i.e. amplify the virus according to the present invention the cell has to be a cell in which the virus is able to replicate such as CEF or BHK cells in the case of recombinant MVA. If it is intended to produce a peptide/protein encoded by the virus, preferably a protein/peptide encoded by a coding sequence, the expression of which is controlled by the ATI promoter or a derivative thereof, the cell may be any cell that can be infected by the recombinant virus and that allows the expression of poxvirus encoded proteins/peptides.

The invention further relates to cells infected with the virus according to the present invention.

SHORT DESCRIPTION OF THE FIGURES

Figure 2:
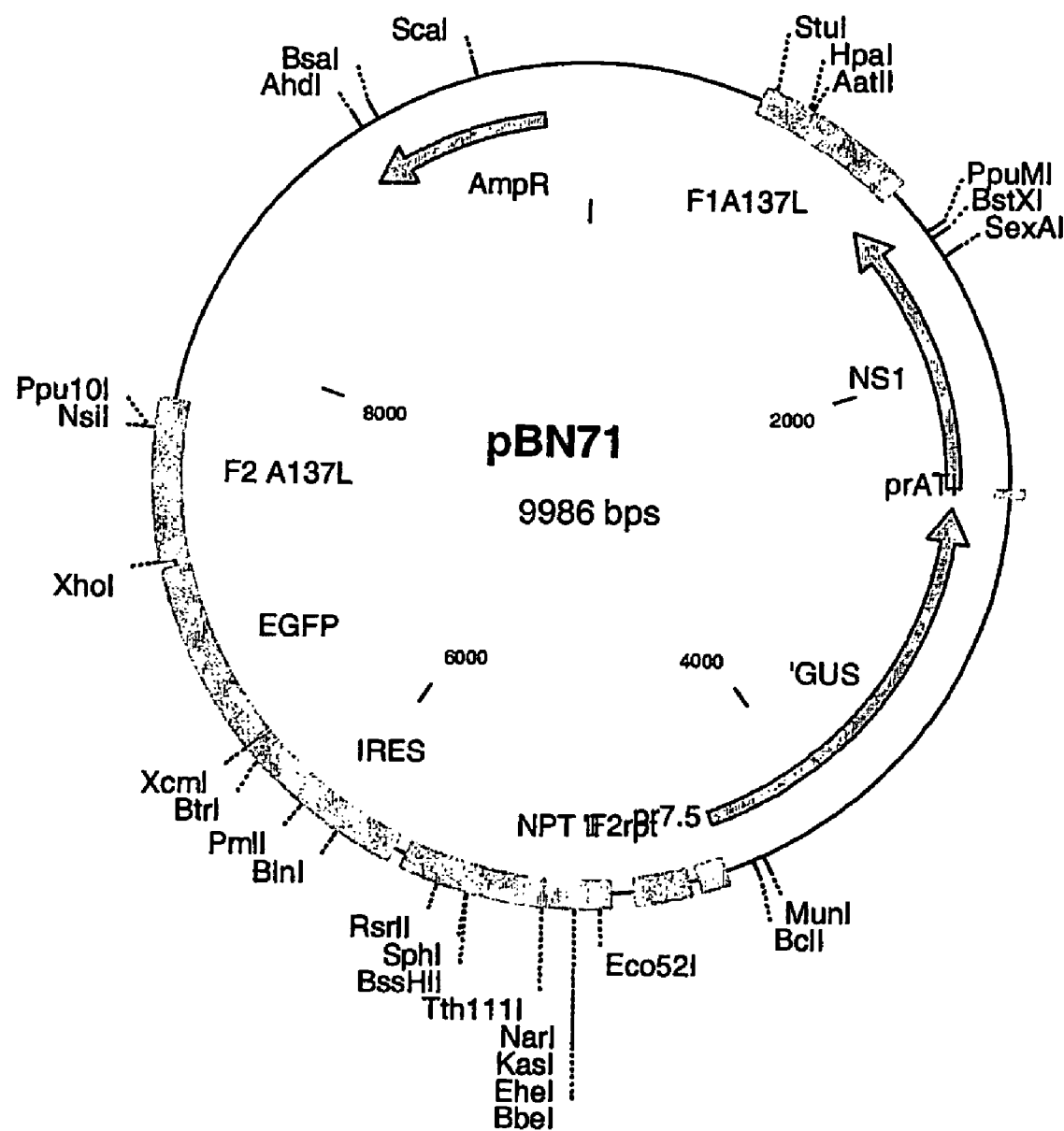

FIG. 1 and FIG. 2: Schematic presentation of the recombination vectors pBN70 (FIG. 1) and pBN71 (FIG. 2) F1A137L=Flank 1 of region of insertion; F2A137L=Flank 2 of region of insertion; F2rpt=repeat of flank2; prATI=ATI promoter; pr7.5=p7.5 promoter; GUS=GUS coding region; NS1=NS1 coding region; NPTII=Neomycin resistance; IRES=internal ribosomal entry site; EGFP=enhanced green fluorescence protein coding region; AmpR=Ampicillin resistance gene.

Figure 3A:
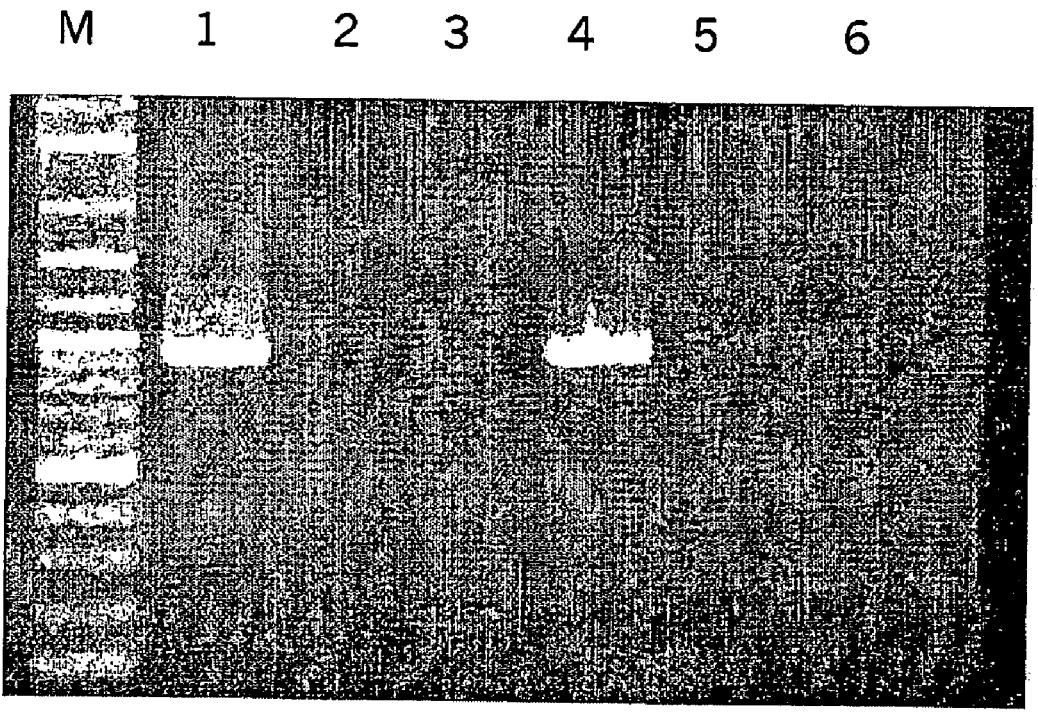
Figure 3B:
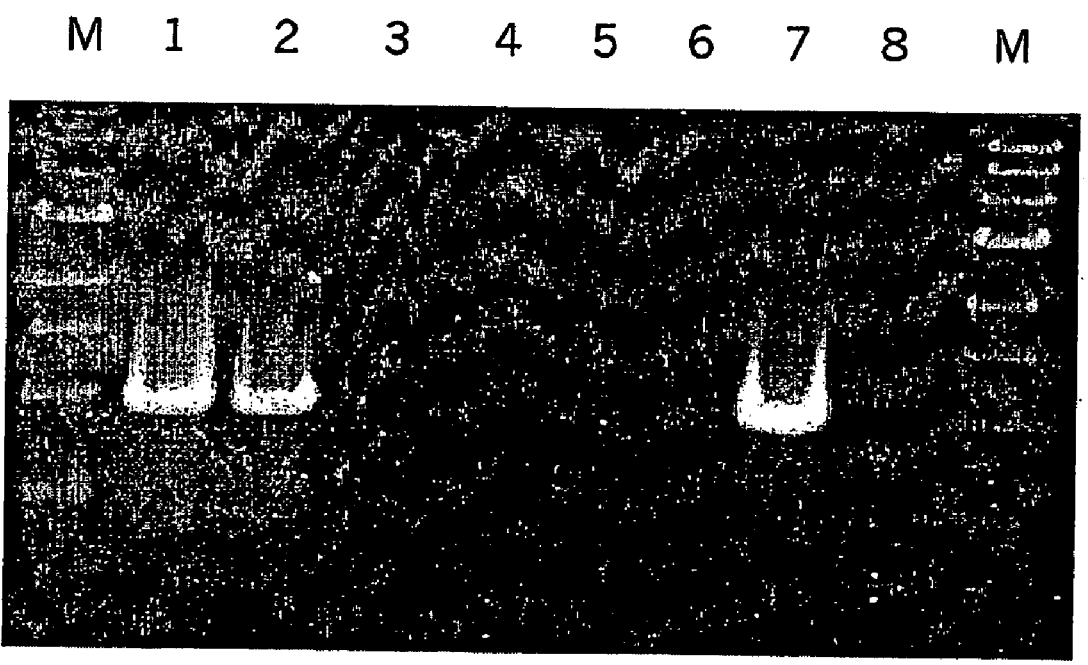

FIG. 3: RT-PCT assay to determine expression of the NS1 gene in cells infected with MVA-mBN30 (FIG. 3A) or MVA-mBN31 (FIG. 3B). In all cases in which a PCR was made the primer were specific for the NS1 gene.

A) M: molecular weight marker; lane 1: assay with plasmid pBN70 (positive control); lane 2: assay without added nucleic acids (negative control); lane 3: PCR with RNA isolated from MVA-mBN30 infected BHK cells without adding reverse transcriptase; lane 4: RT-PCR with RNA isolated from MVA-mBN30 infected BHK cells; lane 5: PCR with RNA isolated from MVA-BN infected BHK cells without adding reverse transcriptase; lane 6: RT-PCR with RNA isolated from MVA-BN infected BHK cells.

B) M: molecular weight marker; lane 1: RT-PCR with RNA from cells infected with mBN31; lane 2: RT-PCR with RNA from cells infected with a different recombinant MVA comprising the NS1 gene in the genome; lane 3: RT-PCR with RNA from MVA-BN infected cells; lane 4: PCR with RNA from cells infected with mBN31 (no reverse transcriptase added); lane 5: PCR with RNA from cells infected with a different recombinant MVA comprising the NS1 gene in the genome (no reverse transcriptase added); lane 6: PCR with RNA from MVA-BN infected cells (no reverse transcriptase added); lane 7: assay with plasmid pBN71 (positive control); lane 8: assay without added nucleic acids (negative control);

EXAMPLE

The following example will further illustrate the present invention. It will be well understood by a person skilled in the art that the provided example in no way may be interpreted in a way that limits the applicability of the technology provided by the present invention to this example.

Stable Insertion of Two Foreign Genes Regulated by the Cowpox ATI Promoter in a Single Site of the MVA Genome The aim of this example was to demonstrate that an insertion of two foreign genes both regulated by the ATI promoter is stable.

Summary:

The following example demonstrates the stability of recombinant MVA comprising two copies of the ATI promoter in the viral genome. To this end the cowpox ATI promoter was fused to the GUS gene (*E. coli* β-Glucuronidase) and non-structural (NS) 1 gene of Dengue virus, respectively. For comparison the GUS gene was also fused to the naturally occurring Vacciniavirus pr7.5 promoter. The ATI promoter-NS1 gene expression cassette and either the ATI promoter-GUS gene expression cassette or the p7.5 promoter-GUS gene expression cassette were inserted into a recombination vector comprising sequences homologous to the MVA genome. (FIGS. 1 and 2). In the resulting plasmids pBN70 (ATI promoter-NS1 gene expression cassette and ATI promoter-GUS gene expression cassette) and pBN71 (ATI promoter-NS1 gene expression cassette and p7.5 promoter-GUS gene expression cassette) the expression cassettes were flanked by sequences homologous to the sequences in the MVA genome in which the expression cassette was to be inserted. The homologous sequences direct the insertion of the expression cassettes into the intergenic region (IGR) 136-137 of the MVA genome. CEF cells were infected with MVA-BN and transfected with pBN70 and pBN71, respectively. In the cells homologous recombination occurred between the MVA genome and the recombination plasmids resulting in recombinant MVA genomes. The recombinants were subjected to several rounds of plaque purification and were passaged in CEF cells (total number of passages including plaque purifications: 20). The recombinants were tested for stability, expression of inserted genes and sequence of recombinant MVA constructs containing two different set-ups of the two promoters. Analysis of the sequence, PCR and functional tests showed that the recombinant fragments are inserted correctly and that the insertions—even when the ATI promoter was inserted twice in the genome—are stable and functional.

Materials and Equipment:

primary CEF cells; MVA-BN with a titre of $10^8$ TCID$_{50}$/ml; Effectene transfection kit (Qiagen); VP-SFM cell culture media (Gibco BRL); G418 (Gibco BRL); DNA Nucleospin Blood Quick Pure Kit (Macherey Nagel); Triple Master DNA polymerase (Eppendorf); Oligos (MWG); Sequencing DCTS Quickstart Kit (Beckman Coulter).

Methods:

The recombination vectors pBN70 and pBN71 (FIGS. 1 and 2) were cloned according to standard protocols known by persons skilled to the art.

$5 \times 10^5$ CEF cells were seeded per transfection reaction in a well of a 6-well-plate and maintained in VP-SFM over night at 37° C. and 5% $CO_2$. The cells were infected with MVA-BN (moi 1.0) in 0.5 ml VP-SFM per well and incubated for 1 h at room temperature on a shaker. Transfection of linearized pBN70 and 71 was performed as described in the manufacturer protocol (Qiagen).

The resulting recombinant viruses were passaged several times under selective conditions (G418, 300 µg/ml) and single plaques were isolated, amplified and analysed until purified clones were generated. The analysed virus finally was passaged 20 times.

Results:

1. Construction of Recombinant Viruses

Two recombinant MVA expressing NS1- and GUS-sequences under control of two different promoter combinations (ATI-NS1/ATI-GUS or ATI-NS1/p7.5-GUS) were created. These sequences together with the selection cassette IRES/EGFP (internal ribosome entry site/enhanced green fluorescent protein) were inserted in 136-137 IGR (intergenic region between ORF A136L and A137L of the MVA genome) site of the MVA genome according to methods known to the person skilled in the art. The viruses were purified and passaged 20 times under selective conditions. Both recombinant MVA were amplified to crude stock scale ($1 \times 175$ cm$^2$ bottle). The ATI promoter sequence in this example correspond to the sequence of SEQ ID.: No. 1.

2. Expression of the EGFP Coding Region

In order to determine functionality of the inserted test gene in the IGR 136-137 fluorescence was observed during passaging. If the inserted gene would not be functional in this site, no expression of EGFP should be detectable. MVA-mBN30 and MVA-mBN31 infected BHK showed clearly that a gene inserted in the 136-137 IGR was transcribed.

3. PCR Analysis of 136-137 IGR of MVA-mBN30 and MVA-mBN31

To exclude possible empty vector contaminations in the IGR 136-137 site and to check whether the viral genome comprises inserts of the expected size a PCR analysis was made. To this end primers were used that bind in the regions flanking the insertion site. The expected PCR bands for primers binding in the flank1 and 2 site are (i) 3.4 kb for the recombinant MVA-mBN30, (ii) 3.5 kb for the recombinant MVA-mBN31 and (iii) 212 bp for the empty vector MVA-BN. Bands of the expected size were found for MVA-mBN30 and MVA-mBN31, indicating that the recombinants had the expected genome structure. No wild-type virus was found in any of the tested MVA-mBN30 or MVA-mBN31DNA preparations. Further, the empty vector control MVA-BN (empty vector) resulted in the expected 212 bp product in both recombinant MVAs. In the negative controls no signal was detected. Thus, an efficient selection and separation of recombinant vector from the empty vector MVA-BN is obtained by selection pressure.

4. Sequencing of Region 136-137

The sequencing results showed that for mBN31 and mBN30 promoters and GUS were inserted without base pair changes in the IGR 136-137 site. For NS1 in mBN30 also no changes in the base pair sequence were found. In mBN31 NS1 had four point mutations in the base pair sequence (position 1315: C instead of G, position 1582: G instead of A, position 1961: A instead of C and position 1963: G instead of T). Two of them (at position 1582 and 1963) resulted in no exchange of amino acids. Irrespective of these minor sequence deviations it is clear from the sequencing results that both recombinants, mBN31 and mBN30, comprise the entire NS1 sequences. Moreover, it can be concluded from the sequencing data that the NS1 gene is stably comprised in the recombinant mBN30 that contains the two ATI promoters. The experiments demonstrate the stability of the recombinant although two identical ATI promoter sequences are included in the viral genome.

5. Analysis of the Expression of the NS1 Gene and the GUS Gene in Recombinants mBN30 and mBN31.

The above described PCR and sequence data have revealed that the NS1 gene and the GUS gene are comprised in the genome of recombinants MVA-mBN30 and 31. To test whether these genes are expressed from the viral genome a RT-PCR of the NS1 region and a functional test and a quantification of the produced GUS proteins were performed.

5.1 RT-PCR of NS1 Region

This experiment was done to demonstrate that the recombinant MVA-mBN30 and mBN31, which both comprise the NS1 gene inserted in the IGR 136-137 site functionally express NS1 as mRNA. BHK cells were infected with the viruses MVA-mBN30 and mBN31, respectively. RNA was isolated from these cells and was used for an RT-PCR assay. The results demonstrate clearly that NS1 is expressed form both viruses in infected BHK-cells. Contamination by viral DNA could be excluded since no PCR signal was detected when the reverse transcription step was omitted. The water control was negative and for the plasmid positive control of both viruses a clear PCR band could be found (FIG. 3).

5.2 Measurement GUS Activity

In order to demonstrate the expression of GUS inserted in MVA-mBN30 and mBN31 after 20 rounds of passaging GUS activity was determined quantitatively. Table 1 shows clearly that GUS was expressed in both recombinant viruses, while no GUS expression could be measured in MVA-BN without insertion.

| Dilution | 1:2 | 1:10 | 1:100 |
|---|---|---|---|
| mBN 30 | 0.968 | 0.224 | 0.022 |
| mBN 31 | 0.414 | 0.089 | 0.012 |
| BN | 0.007 | 0.007 | 0.007 |

Table 1: Measurement of GUS activity in MVA-mBN30, MVA-mBN31 and MVA-BN after 20 passages. MVA-mBN30 and MVA-mBN31 were passaged 20 times in total. Cells were infected with both recombinant viruses and harvested after 24 hours in lysis buffer. GUS activity was measured according to methods known to the person skilled in the art. Values of activity were measured by absorption at 415 nm. Values <0.05 and >2.0 are out of range.

Acceptance Criteria:

PCR Analysis of IGR 136-137

No bands should be observed in the lanes of the negative controls, and only a band of the expected size should be observed in the positive control. For MVA-BN a 212 bp fragment is expected.

Sequencing and PCR of Region 136-137

The PCR amplification of the viral target DNA with the primers should reveal a single fragment of the expected length. The assembling of the sequences should result in one contiguous sequence representing a double-stranded DNA fragment of the expected length. Short single stranded stretches are accepted if no mutation is occurring in this region. Additionally the ends of the contiguous sequence are allowed to be only single stranded due to the heterogeneous nature of PCR amplification products. The sequence of the test sample should show a homology >/=97% to the reference sequence or the respective database sequence.

RT-PCR of NS1

No bands should be observed in the lanes of the negative controls, and only a band of the expected size should be observed in the positive control. For pBN71 a 909 bp fragment and for pBN70 a 907 bp fragment is expected.

CONCLUSION

After 20 passages under selective conditions, PCR analysis of the 136-137 IGR showed no empty vector contamination for MVA-mBN31 (ATI-NS1/p7.5-GUS) or MVA-mBN30 (ATI-NS1/ATI-GUS). For MVA-mBN30 the PCR revealed that no homologous recombination occurred at the ATI site. MVA-mBN30 and mBN31 were tested by (1) final PCR to demonstrate that the stock is free of empty vector and that both genes are still inserted even when both are under the same promoter in the same IGR site (for mBN30), (2) sequencing of the region for demonstrating the unchanged base sequence and (3) functional expression of GUS by a quantitative GUS assay and a RT-PCR for NS1. The results of the study show that the double insertion of two different genes at the same IGR under the control of the same promoter result in no recombination event at the promoter site even after high passage number. Both inserted genes were shown to be expressed.

| Applicant's or agent's file reference number | BN 52 PCT | International application No. |
|---|---|---|

INDICATIONS RELATING TO A DEPOSITED MICROORGANISM (PCT Rule 13bis)

A. The indications made below relate to the microorganism referred to in the description
on page ____4____ , line ____28____ .

B. IDENTIFICATION OF DEPOSIT  Further deposits are identified on an additional sheet ☐

Name of depositary institution  ECACC
European Collection of Cell Cultures

Address of depositary institution (including postal code and country)
Centre for Applied Microbiology & Research
Salisbury
Wiltshire SP4 OJG
United Kingdom

| Date of deposit | Accession Number |
|---|---|
| August 30, 2000 | 00083008 |

C. ADDITIONAL INDICATIONS (leave blank if not applicable)  This information is continued on an additional sheet ☐

In respect of all designated States to which such action is possible and to the extent that it is legally permissable under the law of the designated State, it is requested that a sample of the deposited microorganism be made available only by the issue thereof to an independent expert, in accordance with the relevant patent legislation, e.g., EPC Rule 28 (4); UK Patent Rules 1995, Schedule 2, Paragraph 3; Australian Regulation 3.25(3); Danish Patents Act Sections 22 and 33(3) and generally similar provisions mutatis mutandis for any other designated State.

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g. "Accession Number of Deposit")

| For receiving Office use only | For International Bureau use only |
|---|---|
| ☒ This sheet was received with the international application | ☐ This sheet was received by the International Bureau on: |
| Authorized officer  L. Bonomelli | Authorized officer |

Form PCT/RO/134 (July 1992)

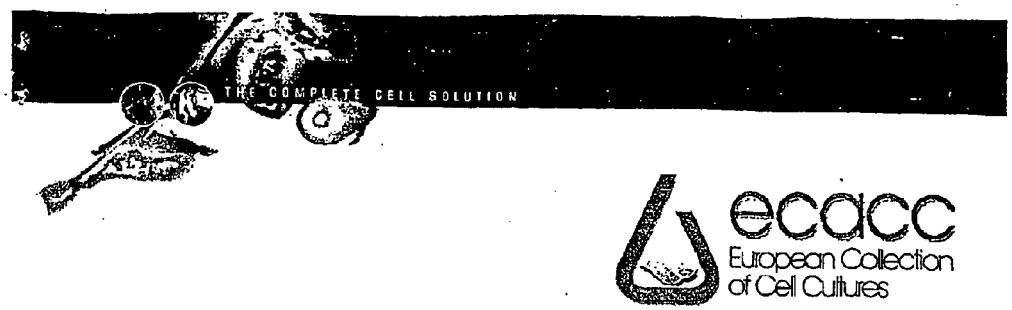

Centre for Applied Microbiology and Research
&
European Collection of Cell Cultures This document certifies that Virus
(Deposit Ref. V00083008) has been accepted as a patent deposit,
in accordance with
The Budapest Treaty of 1977,
with the European Collection of Cell Cultures on 30$^{TH}$ August 2000

Dr P J Packer
Quality Manager, ECACC

CAMR  European Collection of Cell Cultures, CAMR, Salisbury, Wiltshire SP4 0JG UK.
Tel: 44 (0) 1980 612512  Fax: 44 (0) 1980 611315  Email: ecacc@camr.org.uk  Web Site: ecacc.org.uk Appendix 3

Page 25

| IV. CONDITIONS UNDER WHICH THE VIABILITY TEST HAS BEEN PERFORMED [4] |
|---|
| V00083008 - MVA-BN<br><br>VIABILITY OF MVA-BN WAS TESTED BY GROWING THE VIRUS ON BHK CELLS AND CALCULATING THE TCD50. |

| V. INTERNATIONAL DEPOSITARY AUTHORITY | |
|---|---|
| Name: Dr P J Packer<br>      ECACC CAMR<br>Address: Porton Down<br>      Salisbury<br>      Wiltshire<br>      SP4 0JG | Signature(s) of person(s) having the power to represent the International Depositary Authority or of authorized official(s):<br><br>Date: 14/12/00    P Slade |

[4] Fill in if the information has been requested and if the results of the test were negative.

APPENDIX 3

Page 24

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

TO

BAVARIAN NORDIC RESEARCH
INSTITUTE GMBH
FRAUNHOFERSTRASSE 18B
D-82152 MARTINSRIED
GERMANY

VIABILITY STATEMENT
Issued pursant to Rule 10.2 by the
INTERNATIONAL DEPOSITARY AUTHORITY
identified on the following page

NAME AND ADDRESS OF THE PARTY
TO WHOM THE VIABILITY OF STATEMENT
IS ISSUED

| I. DEPOSITOR | II. IDENTIFICATION OF THE MICROORGANISM |
|---|---|
| Name: BAVARIAN NORDIC RESEARCH INSTITUTE GMBH<br><br>Address: FRAUNHOFERSTRASSE 18B<br>D-82152.MARTINSRIED<br>GERMANY | Accession number given by the INTERNATIONAL DEPOSITORY AUTHORITY:<br><br>V00083008<br><br>Date of the deposit or of the transfer:<br>30$^{TH}$ August 2000 |

| II. VIABILITY STATEMENT |
|---|
| The viability of the microorganism identified under II above was tested on ¹. On that date, the said microorganism was<br><br>[X] ³ viable<br><br>[ ] ² no longer viable |

1  Indicate the date of the original deposit or, where a new deposit or a transfer has been made, the most relevant date (date of the new deposit or date of the transfer).

2  In the cases referred to in Rule 10.2 (a) (ii) and (iii), refer to the most recent viability test.

3  Mark with a cross the applicable box.

APPENDIX 3

Page 14

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

TO

BAVARIAN NORDIC RESEARCH
INSTITUTE GMBH
FRAUNHOFERSTRASSE 18B
D-82152 MARTINSRIED
GERMANY

NAME AND ADDRESS OF DEPOSITOR

| I. IDENTIFICATION OF THE MICROORGANISM | |
|---|---|
| Identification reference given by the DEPOSITOR: | Accession number given by the INTERNATIONAL DEPOSITARY AUTHORITY: |
| MVA-BN | V00083008 |

II. SCIENTIFIC DESCRIPTION AND/OR PROPOSED TAXONOMIC DESIGNATION

The microorganism identified under I above was accompanied by:

[X] A scientific description

[ ] A proposed taxonomic designation (Mark with a cross where applicable)

III. RECEIPT AND ACCEPTANCE

This International Depository Authority accepts the microorganism identified under I above, which was received by it on 30th August 2000 (date of the original deposit)[1]

IV. RECEIPT OF REQUEST FOR CONVERSION

The microorganism identified under I above was received by this International Depository Authority on              (date of the original deposit) and
A request to convert the original deposit to a deposit under the Budapest Treaty
was received by it on              (date of receipt of request for conversion)

IV. INTERNATIONAL DEPOSITORY AUTHORITY

| Name: Dr P J Packer | Signature(s) of person(s) having the power to represent the International Depository Authority or of authorized officials(s): |
|---|---|
| Address: ECACC CAMR Porton Down Salisbury SP4 OJG | Date: PSPacker 14/12/00 |

[1] Where Rule 6.4(d) applies, such date is the date on which the status of international depositary authority was acquired Form BP/4 (sole page)

1991

Certificate of Analysis

Product Description  MVA-BN
Accession Number  00083008

---

Test Description:  The Detection of Mycoplasma by Isolation on Mycoplasma Pig Serum Agar and in Mycoplasma Horse Serum Broth.
SOP QC/MYCO/01/02

Acceptance Criterion/Specification:  All positive controls (*M. pneumoniae* & *M. orale*) must show evidence of mycoplasma by typical colony formation on agar plates. Broths are subcultured onto Mycoplasma Pig Serum Agar where evidence of mycoplasma by typical colony formation is evaluated. All negative control agar plates must show no evidence of microbial growth.
The criteria for a positive test result is evidence of mycoplasma by typical colony formation on agar. A negative result will show no such evidence.

Test Number:  21487

Date:  27/11/00

Result:

| | |
|---|---|
| Positive Control: | Positive |
| Negative Control: | Negative |
| Test Result: | Negative |
| Overall Result: | PASS |

---

Test Description:  Detection of Mycoplasma using a Vero indicator cell line and Hoechst 33258 fluorescent detection system.
SOP QC/MYCO/07/05

Acceptance Criterion/Specification:  The Vero cells in the negative control are clearly seen as fluorescing nuclei with no cytoplasmic fluorescence. Positive control (*M. orale*) must show evidence of mycoplasma as fluorescing nuclei plus extra nuclear fluorescence of mycoplasma DNA. Positive test results appear as extra nuclear fluorescence of mycoplasma DNA. Negative results show no cytoplasmic fluorescence.

Test Number:  21487

Date:  27/11/00

Result:

| | |
|---|---|
| Positive Control: | Positive |
| Negative Control: | Negative |
| Test Result: | Negative |
| Overall Result: | PASS |

---

Authorised by.................................ECACC, Head of Quality.............. Date

Certificate of Analysis

Product Description     MVA-BN
Accession Number        00083008

---

Test Description:   Detection of bacteria and fungi by isolation on Tryptone Soya Broth (TSB) and in Fluid Thioglycollate Medium (FTGM). SOP QC/BF/01/02

Acceptance Criterion/Specification: All positive controls (*Bacillus subtilus*, *Clostridium sporogenes* and *Candida albicans*) show evidence of microbial growth (turbidity) and the negative controls show no evidence of microbial growth (clear).
The criteria for a positive test is turbidity in any of the test broths. All broths should be clear for negative test result.

Test Number: 21487
Date: 27/11/00
Result:

| | |
|---|---|
| Positive Control: | Positive |
| Negative Control: | Negative |
| Test Result: | Negative |
| Overall Result: | PASS |

Test Description:   Determination of $TCID_{50}$ of cytopathic Virus titration. (SOP ECACC/055) Cell Acceptance Criterion/Specification/Criteria: Negative controls should show no sign of Cytopathic effects. The Test Sample is serially diluted into in 4 wells of indicator cell lines for each dilution. Cytopathic effects indicate that virus is present. Virus titre is calculated using the below equation where x is the value obtained from a standard $TCID_{50}$ Table as a result of the distribution of the wells displaying less than 4 positive wells per dilution, and y is the value of the highest dilution where all 4 wells are positive:

$$TCID_{50} = \frac{1}{y} \times 10^{1+x}$$

Date: 01/12/00

Result:

| | |
|---|---|
| Indicator Cell Line: | BHK21 (Clone 13) |
| Negative Control: | NO CPE |
| Test Sample: | CPE |
| Distribution of less that 4 positive wells: | 4, 4, 4, 3, 0 |
| X: | 1.25 |
| Y: | $10^{-3}$ |

$$TCID_{50} = \frac{1}{10^{-7}} \times 10^{1+01.25}$$

$$= 10^{8.25}$$

| | |
|---|---|
| Overall Result: | Virus Present |

* End of Certificate *

Authorised by..................................ECACC, Head of Quality.............. Date

| | ECACC use only |
|---|---|
| | Accession No: |
| | Depositors Code: |

*Patent Deposit Accession Form - Virus*

DEPOSITOR INFORMATION

Name of Depositor/Company/Institute __Bavarian Nordic Research Institute GmbH__

*(NB this will be the name that appears on certification)*

Contact Name __Dr. Paul M. Howley__, ~~Dr. Petra Pielken~~

Depositor Address __Fraunhoferstraße 18b, D-82152 Martinsried, Germany__

Tel No __++49 89 8565 0030__    Fax No __++49 89 8565 1333__

BIOHAZARD STATEMENT MUST BE ENCLOSED

*The deposit is made in accordance with the terms of the Budapest Treaty 1977. I agree to abide by the conditions and regulations regarding deposits of cell lines to the ECACC.*

Signature __P. Pielken__    Date __25.08.2000__

Address to which invoice should be sent (if different from above)

__Accounts Department, Bavarian Nordic Research Institute GmbH__
__Fraunhoferstraße 18b__
__D-81152 Martinsried, Germany__

VIRUS INFORMATION

Name in full    __Modified Vaccinia Virus Ankara__
Abbreviated Name __MVA-BN__    Identification on Ampoules __Lot 010500__
Strain _____    Viral #  __2, 32, 51, 76, 82, 85__
Normal Host __None__    Serological Type __84, 88, 98, 99, 106__
Virus Titre Deposited __10⁹__

VIRUS PROPAGATION

Host cells (first choice) __Chicken Embryo Fibroblast (CEF)__
Alternative Host Cells __-__

Details of Host Cell Growth (media, temperature, seeding density, growth factors etc)
__Chicken Embryo Fibroblast Cultured in RPMI Media Supplemented with 10% FCS.__
__AT 37°C/5%CO2. No Growth Factors Needed.__

Details of Virus Growth (eg confluency of host cells, co-cultivation, moi, effects, time taken)
__Infect CEF Cell At Near Cell Confluency (Approx. 90%) At MOI 0,1 TCID50/Cell__

VIRUS STORAGE    Confluency; Infection Times on Average 3 days At 37°C/5%CO2
Material stored (eg supernatant, infected cell extract, viable infected cells etc)
Temperature and conditions  Infected Cell Extract At-80°C

VIRUS ASSAY

Method (enclose if necessary)
__Does not form Plaques. It forms Foci of CPE in CEF Monolayers. Titrate by__

LITERATURE REFERENCES (if any)   TCID50 Method - Reference:    Vol 35:
__Ingo Drexler et al. 2000__ ~~in Methods in Molecular Medicine~~

ANY OTHER RELEVANT INFORMATION  Gene Therapy: Methods and Protocols Ed. W. Walther
                                 and U. Stein. Human Press
__Virus Looses Viability At Low pH. Dilute Virus With Sterile__
__1MM Tris-Hcl pH9 Buffer__

European Collection of Cell Cultures, Centre for Applied Microbiology & Research
Salisbury, Wiltshire SP4 0JG, UK.
*Tel:* +44 1980 612513 *Fax:* +44 1980 611315
*E.Mail:* ecacc@camr.org.uk *Web Site:* www.camr.org.uk

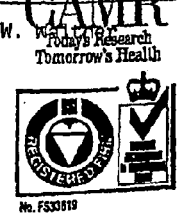

ECACC use only
Accession No:
Depositors Code:

BIOHAZARD STATEMENT

*(To be included with all deposits)*

Deposit category

Cell Culture ☐   Plant Culture ☐   Virus Recombinant DNA ☐   DNA Probe ☐   Bacteria ☐

Does the above deposit represent an infectious, toxic or allergenic hazard?   Yes ☐   No ☒

If yes, please give details and any associated hazard category (eg. ACDP category) and fax to ECACC PRIOR to shipment of cells.

_____
_____
_____

Does the above deposit contain genetically manipulated material?   Yes ☐   No ☒

If yes, please enclose a general description and answer the following:

a.  Is the material   DNA ☐   RNA ☐
b.  Is the material present in a host organism?   Yes ☐   No ☐
c.  Is the genetic material readily transferred to environmental organisms?   Yes ☐   No ☐
d.  Is the genetic material likely to be expressed as protein?   Yes ☐   No ☐
e.  what is the category of this material under ACGM regulations?

ie,   i. containment level _____
         ii. GMO type _____

For any positive responses to questions b-d please give details

_____
_____
_____

Please supply any further details which would be relevant to assessing the safe handling conditions for materials to be deposited at ECACC.

___Highly attentuated Replication Incompetent in Humans and Animals___
_____

Signed _P. Pielken_   Date _26.08.2000_

Print name   Dr. Petra Pielken

*Please note that deposits which are, or contain, animal pathogens require an import licence into the EC. Please allow 8 weeks for this pro submit information requested by ECACC for licence applications as quickly as possible.*

CAMR
Today's Research
Tomorrow's Health

European Collection of Cell Cultures, Centre for Applied Microbiology & Research
Salisbury, Wiltshire SP4 0JG, UK.
Tel: +44 1980 612512  Fax: +44 1980 611315
E.Mail: ecacc@camr.org.uk  Web Site: www.camr.org.uk

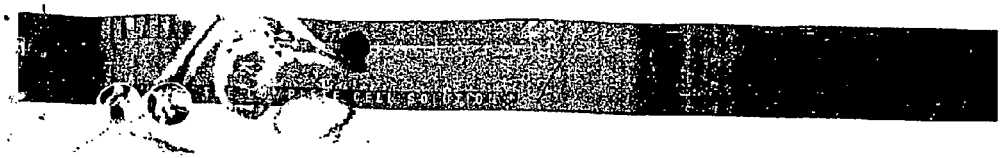

Centre for Applied Microbiology and Research
&
European Collection of Cell Cultures This document certifies that Virus
(Deposit Ref. V00120707) has been accepted as a patent deposit,
in accordance with
The Budapest Treaty of 1977,
with the European Collection of Cell Cultures on 7TH December 2000

Dr P J Packer
Quality Manager, ECACC

European Collection of Cell Cultures, CAMR, Salisbury, Wiltshire SP4 0JG UK.
Tel: 44 (0) 1980 612512  Fax: 44 (0) 1980 611315  Email: ecacc@camr.org.uk  Web Site: ecacc.org.uk

APPENDIX 3

Page 14

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

TO
BAVARIAN NORDIC RESEARCH
INSTITUTE GMBH
FRAUNHOFERSTRASSE 18B
D-82152 MARTINSRIED
GERMANY

NAME AND ADDRESS
OF DEPOSITOR

I. IDENTIFICATION OF THE MICROORGANISM

Identification reference given by the DEPOSITOR:

MVA-575

Accession number given by the INTERNATIONAL DEPOSITARY AUTHORITY:

V00120707

II. SCIENTIFIC DESCRIPTION AND/OR PROPOSED TAXONOMIC DESIGNATION

The microorganism identified under I above was accompanied by:

[X] A scientific description

[ ] A proposed taxonomic designation (Mark with a cross where applicable)

III. RECEIPT AND ACCEPTANCE

This International Depository Authority accepts the microorganism identified under I above, which was received by it on 7TH December 2000 (date of the original deposit)[1]

IV. RECEIPT OF REQUEST FOR CONVERSION

The microorganism identified under I above was received by this International
Depository Authority on                    (date of the original deposit) and
A request to convert the original deposit to a deposit under the Budapest Treaty
was received by it on                      (date of receipt of request for conversion)

IV. INTERNATIONAL DEPOSITORY AUTHORITY

Name: Dr P J Packer

Address:   ECACC
           CAMR
           Porton Down
           Salisbury SP4 0JG Signature(s) of person(s) having the power to represent the International Depository Authority or of authorized officials(s):

Date:

1 Where Rule 6.4(d) applies, such date is the date on which the status of international depository authority was acquired Form BP/4 (sole page)                                                                           1991

APPENDIX 3

Page 24

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

TO

BAVARIAN NORDIC RESEARCH
INSTITUTE GMBH
FRAUNHOFERSTRASSE 18B
D-82152 MARTINSRIED
GERMANY

VIABILITY STATEMENT
Issued pursant to Rule 10.2 by the
INTERNATIONAL DEPOSITARY AUTHORITY
identified on the following page

NAME AND ADDRESS OF THE PARTY
TO WHOM THE VIABILITY OF STATEMENT
IS ISSUED

| I. DEPOSITOR | II. IDENTIFICATION OF THE MICROORGANISM |
|---|---|
| Name: BAVARIAN NORDIC RESEARCH INSTITUTE GMBH | Accession number given by the INTERNATIONAL DEPOSITORY AUTHORITY: |
| Address: FRAUNHOFERSTRASSE 18B D-82152 MARTINSRIED GERMANY | 00120707<br><br>Date of the deposit or of the transfer: 7$^{TH}$ December 2000 |

II. VIABILITY STATEMENT

The viability of the microorganism identified under II above was tested on [1]. On that date, the said microorganism was

[ ] [3] viable

[ ] [3] no longer viable

1     Indicate the date of the original deposit or, where a new deposit or a transfer has been made, the most relevant date (date of the new deposit or date of the transfer).

2     In the cases referred to in Rule 10.2 (a) (ii) and (iii), refer to the most recent viability test.

3     Mark with a cross the applicable box.

Appendix 3

Page 25

| IV. CONDITIONS UNDER WHICH THE VIABILITY TEST HAS BEEN PERFORMED |
|---|
| MVA-575 - V00120707<br><br>THIS VIRUS WAS TITRATED ON BHK CELLS TCID$_{50}$ = $10^{6.5}$ |

| V. INTERNATIONAL DEPOSITARY AUTHORITY | |
|---|---|
| Name: Dr P J Packer<br>　　　　ECACC CAMR<br>Address: Porton Down<br>　　　　Salisbury<br>　　　　Wiltshire<br>　　　　SP4 0JG | Signature(s) of person(s) having the power to represent the International Depositary Authority or of authorized official(s):<br><br>Date: 23/3/01 |

4 Fill in if the information has been requested and if the results of the test were negative.

Certificate of Analysis

Product Description     MVA-575
Accession Number     00120707

---

Test Description:    Determination of $TCID_{50}$ of cytopathic Virus titration. (SOP ECACC/055) Cell Acceptance Criterion/Specification/Criteria: Negative controls should show no sign of Cytopathic effects. The Test Sample is serially diluted into in 4 wells of indicator cell lines for each dilution. Cytopathic effects indicate that virus is present. Virus titre is calculated using the below equation where x is the value obtained from a standard $TCID_{50}$ Table as a result of the distribution of the wells displaying less than 4 positive wells per dilution, and y is the value of the highest dilution where all 4 wells are positive:

$$TCID_{50} = \frac{1}{y} \times 10^{1+x}$$

Date:    19/01/01
Result:

| | |
|---|---|
| Indicator Cell Line: | BHK 21 CLONE 13 |
| Negative Control: | NO CPE |
| Test Sample: | CPE |
| Distribution of less that 4 positive wells: | 4, 4, 0 |
| X: | 0.50 |
| Y: | $10^{-5}$ |

$$TCID_{50} = \frac{1}{10^{-5}} \times 10^{1+0.50}$$

$$= 10^{6.5}$$

Overall Result:    Virus Present

---

Test Description:    The Detection of Mycoplasma by Isolation on Mycoplasma Pig Serum Agar and in Mycoplasma Horse Serum Broth.
SOP QC/MYCO/01/02

Acceptance Criterion/Specification:    All positive controls (*M. pneumoniae* & *M. orale*) must show evidence of mycoplasma by typical colony formation on agar plates. Broths are subcultured onto Mycoplasma Pig Serum Agar where evidence of mycoplasma by typical colony formation is evaluated. All negative control agar plates must show no evidence of microbial growth.

The criteria for a positive test result is evidence of mycoplasma by typical colony formation on agar. A negative result will show no such evidence.

Test Number:    21702
Date:    12/02/01
Result:

| | |
|---|---|
| Positive Control: | Positive |
| Negative Control: | Negative |
| Test Result: | Negative |
| Overall Result: | PASS |

---

Authorised by......................................ECACC, Head of Quality................ Date

Certificate of Analysis

Product Description  MVA-575
Accession Number  00120707

Test Description: Detection of Mycoplasma using a Vero indicator cell line and Hoechst 33258 fluorescent detection system.
SOP QC/MYCO/07/05

Acceptance Criterion/Specification: The Vero cells in the negative control are clearly seen as fluorescing nuclei with no cytoplasmic fluorescence. Positive control (*M. orale*) must show evidence of mycoplasma as fluorescing nuclei plus extra nuclear fluorescence of mycoplasma DNA. Positive test results appear as extra nuclear fluorescence of mycoplasma DNA. Negative results show no cytoplasmic fluorescence.

Test Number: 21702

Date: 12/02/01

Result:

| | |
|---|---|
| Positive Control: | Positive |
| Negative Control: | Negative |
| Test Result: | Negative |
| Overall Result: | PASS |

Test Description: Detection of bacteria and fungi by isolation on Tryptone Soya Broth (TSB) and in Fluid Thioglycollate Medium (FTGM). SOP QC/BF/01/02

Acceptance Criterion/Specification: All positive controls (*Bacillis subtilus*, *Clostridium sporogenes* and *Candida albicans*) show evidence of microbial growth (turbidity) and the negative controls show no evidence of microbial growth (clear).
The criteria for a positive test is turbidity in any of the test broths. All broths should be clear for negative test result.

Test Number: 21702

Date: 12/02/01

Result:

| | |
|---|---|
| Positive Control: | Positive |
| Negative Control: | Negative |
| Test Result: | Negative |
| Overall Result: | PASS |

Authorised by................................ECACC, Head of Quality...............Date

Patent Deposit Accession Form - Virus

DEPOSITOR INFORMATION

Name of Depositor/Company/Institute: Bavarian Nordic Research Institute GmbH
(NB this will be the name that appears on certification)
Contact Name: Dr. Paul Howley, Dr. Petra Pielken
Depositor Address: Fraunhoferstraße 18b, D-82152 Martinsried, Germany
Tel No: 89 8565 0030    Fax No: ++49 89 8565 1333

BIOHAZARD STATEMENT MUST BE ENCLOSED

*The deposit is made in accordance with the terms of the Budapest Treaty 1977. I agree to abide by the conditions and regulations regarding deposit of cell lines to the ECACC.*

Signature: P. Pielken    Date: 05.12.2000

Address to which invoice should be sent (if different from above):
Accounts Department, Bavarian Nordic Research Institute GmbH
Fraunhoferstraße 18b
D-82152 Martinsried, Germany

VIRUS INFORMATION

Name in full: Modified Vaccinia Virus Ankara
Abbreviated Name: MVA           Identification on Ampoules:
Strain: No. 575                 Serological Type:
Normal Host: None
Virus Titre Deposited:

VIRUS PROPAGATION

Host cells (first choice): Chicken Embryo Fibroblast (CEF)
Alternative Host Cells:
Details of Host Cell Growth (media, temperature, seeding density, growth factors etc):
Chicken Embryo Fibroblast Cultured in RPMI Media Supplemented with 10% FCS. AT 37°C/5%CO2. No Growth Factors Needed.

Details of Virus Growth (eg confluency of host cells, co-cultivation, moi, effects, time taken):
Infect CEF Cell At Near Cell Confluency (Approx. 90%) At MOI 0.1 TCID50/Cell Confluency; Infection Times on Average 3 Days At 37°C/5%CO2

VIRUS STORAGE
Material stored (eg supernatant, infected cell extract, viable infected cells etc)
Temperature and conditions: Infected Cell Extract, At -80°C

VIRUS ASSAY

Method (enclose if necessary):
Does not form Plaques. It forms Foci of CPE in CEF Monolayers. Titrate by TCID50 Method - Reference:

LITERATURE REFERENCES (if any): Ingo Drexler et al. 2000 in Methods in Molecular Medicine Vol 35;

ANY OTHER RELEVANT INFORMATION: Gene Therapy: Methods and Protocols. Ed. W. Walther and U. Stein. Human Press Virus Looses Viability At Low pH. Dilute Virus With Sterile 1MM Tris-Hcl pH9 Buffer European Collection of Cell Cultures, Centre for Applied Microbiology & Research
Salisbury, Wiltshire SP4 0JG, UK.
Tel: +44 1980 612512  Fax: +44 1980 611315
E.Mail: ecacc@camr.org.uk  Web Site: www.camr.org.uk

BIOHAZARD STATEMENT

*(To be included with all deposits)*

Deposit category

Cell Culture ☐   Plant Culture ☐   Virus Recombinant DNA ☐   DNA Probe ☐   Bacteria ☐

Does the above deposit represent an infectious, toxic or allergenic hazard?   Yes ☐   No ☒

If yes, please give details and any associated hazard category (eg. ACDP category) and fax to ECACC PRIOR to shipment of cells.

MVA is classified into biosafety level 1 (S1) by ZKBS

File No.: 6790-10-14

Date: May 1997

Does the above deposit contain genetically manipulated material?   Yes ☐   No ☒

If yes, please enclose a general description and answer the following:

a. is the material                                                         DNA ☐      RNA ☐
b. is the material present in a host organism?                             Yes ☐      No ☐
c. is the genetic material readily transferred to environmental organisms? Yes ☐      No ☐
d. is the genetic material likely to be expressed as protein?              Yes ☐      No ☐
e. what is the category of this material under ACGM regulations?

ie,   i. containment level _____ ii. GMO type _____

For any positive responses to questions b-d please give details

_____

_____

_____

Please supply any further details which would be relevant to assessing the safe handling conditions for materials to be deposited at ECACC.

_____

_____

Signed _P. Pielken_                                     Date: 05 12 20__

Print name  Dr. Petra Pielken

*Please note that deposits which are, or contain, animal pathogens require an import licence into the EC. Please allow 8 weeks for this proces: submit information requested by ECACC for licence applications as quickly as possible.*

CAMR
Today's Research
Tomorrow's Health

European Collection of Cell Cultures, Centre for Applied Microbiology & Research
Salisbury, Wiltshire SP4 0JG, UK.
Tel: +44 1980 612512  Fax: +44 1980 611815
E.Mail: ecacc@camr.org.uk  Web Site: www.camr.org.uk

| Applicant's or agent's file reference number | BN 52 PCT | International application No. |
|---|---|---|

INDICATIONS RELATING TO A DEPOSITED MICROORGANISM (PCT Rule 13bis)

A. The indications made below relate to the microorganism referred to in the description
on page ____4____, line ____27____.

B. IDENTIFICATION OF DEPOSIT  Further deposits are identified on an additional sheet ☐

Name of depositary institution ECACC
European Collection of Cell Cultures

Address of depositary institution (including postal code and country)
Centre for Applied Microbiology & Research, CAMR
Porton Down
Salisbury, SP4 OJG
United Kingdom

| Date of deposit | Accession Number |
|---|---|
| January 27, 1994 | 94012707 |

C. ADDITIONAL INDICATIONS (leave blank if not applicable)  This information is continued on an additional sheet ☐

In respect of all designated States to which such action is possible and to the extent that it is legally permissable under the law of the designated State, it is requested that a sample of the deposited microorganism be made available only by the issue thereof to an independent expert, in accordance with the relevant patent legislation, e.g., EPC Rule 28 (4); UK Patent Rules 1995, Schedule 2, Paragraph 3; Australian Regulation 3.25(3); Danish Patents Act Sections 22 and 33(3) and generally similar provisions mutatis mutandis for any other designated State.

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g., "Accession Number of Deposit")

---
For receiving Office use only
☒ This sheet was received with the International application Authorized officer
L. Bonomelli ---
For International Bureau use only
☐ This sheet was received by the International Bureau on:

Authorized officer

Form PCT/RO/134 (July 1992)

PHLS Public Health Laboratory Service

Centre for Applied Microbiology and Research

This document certifies that Virus Strain
(Deposit ref V94012707 ) has been accepted
as a patent deposit, in accordance with
The Budapest Treaty of 1977,
with the European Collection of Animal Cell Cultures on
27th January 1994

Dr. Alan Doyle,
Curator.

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

TO
Prof Dr Dr h.c. mult
Anton Mayr
Bockmeyrstrasse 9
80992 Munchen
Germany
NAME AND ADDRESS OF DEPOSITOR RECEIPT IN THE CASE OF AN ORIGINAL DEPOSIT
issued pursuant to Rule 7.1 by the
INTERNATIONAL DEPOSITARY AUTHORITY
identified at the bottom of this page

---

I. IDENTIFICATION OF THE MICROORGANISM

Identification reference given by the DEPOSITOR:

Vacciniavirus Strain MVA

Accession number given by the INTERNATIONAL DEPOSITARY AUTHORITY:

V94012707

---

II. SCIENTIFIC DESCRIPTION AND/OR PROPOSED TAXONOMIC DESIGNATION

The microorganism identified under I above was accompanied by:

[X] a scientific description

[ ] a proposed taxonomic designation (Mark with a cross where applicable)

---

III. RECEIPT AND ACCEPTANCE

This International Depositary Authority accepts the microorganism identified under I above, which was received by it on 27/1/94 (date of the original deposit)[1]

---

IV. RECEIPT OF REQUEST FOR CONVERSION

The microorganism identified under I above was received by this International Depositary Authority on _____ (date of the original deposit) and a request to convert the original deposit to a deposit under the Budapest Treaty was received by it on _____ (date of receipt of request for conversion)

---

V. INTERNATIONAL DEPOSITARY AUTHORITY

Name: Dr A. Doyle

Address: ECACC, CAMR
Porton Down
Salisbury, SP4 0JG, UK

Signature(s) of person(s) having the power to represent the International Depositary Authority or of authorized official(s):

Date: 28th June 1994

---

[1] Where Rule 6.4(d) applies, such date is the date on which the status of international depositary authority was acquired.

Form BP/4 (sole page)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

TO
Prof Dr Dr h.c. mult Anton Mayr
Bockmeyrstrasse 9
80992 Munchen
Germany

VIABILITY STATEMENT
issued pursuant to Rule 10.2 by the
INTERNATIONAL DEPOSITARY AUTHORITY
identified on the following page

NAME AND ADDRESS OF THE PARTY
TO WHOM THE VIABILITY STATEMENT
IS ISSUED

| I. DEPOSITOR | II. IDENTIFICATION OF THE MICROORGANISM |
|---|---|
| Name: Prof Dr Dr h.c. mult Anton Mayr<br><br>Address: Bockmeyrstrasse 9<br>80992 Munchen<br>Germany | Accession number given by the<br>INTERNATIONAL DEPOSITARY AUTHORITY:<br>V94012707<br><br>Date of the deposit or of the transfer:<br>27th January 1994 |

III. VIABILITY STATEMENT

The viability of the microorganism identified under II above was tested
on     27th January 1994 [1]     [2]. On that date, the said microorganism was

[X] viable [3]

[ ] no longer viable [3]

[1] Indicate the date of the original deposit or, where a new deposit or a transfer has been made, the most recent relevant date (date of the new deposit or date of the transfer).

[2] In the cases referred to in Rule 10.2(a)(ii) and (iii), refer to the most recent viability test.

[3] Mark with a cross the applicable box.

Form BP/9 (first page)

| IV. CONDITIONS UNDER WHICH THE VIABILITY TEST HAS BEEN PERFORMED[4] |
|---|
| |

| V. INTERNATIONAL DEPOSITARY AUTHORITY | |
|---|---|
| Name: Dr A. Doyle<br><br>Address: ECACC<br>CAMR<br>Porton Down<br>Salisbury, SP4 OJG, UK. | Signature(s) of person(s) having the power to represent the International Depositary Authority or of authorized official(s):<br>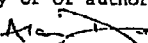<br>Date: 28th June 1994 |

[4] Fill in if the information has been requested and if the results of the test were negative.

The invention claimed is:

1. Recombinant poxvirus comprising in the viral genome at least two expression cassettes, each comprising a cowpox ATI promoter according to SEQ ID NO:1, a polynucleotide sequence in which not more than 6 nucleotides are substituted, deleted, and/or inserted into SEQ ID. NO:1, said sequence including nucleotides 25 through 29 of SEQ ID NO:1 and still active as an ATI promoter, or a polynucleotide comprising at least 10 nucleotides including nucleotides 25 to 29 of SEQ ID NO: 1 and still active as an ATI promoter and a coding sequence, wherein the expression of the coding sequence is regulated by said promoter or said polynucleotides.

2. Recombinant poxvirus according to claim 1, wherein the Cowpox ATI promoter has the biological activity of being active as a Vaccinia virus late promoter.

3. Recombinant poxvirus according to claim 1, wherein the Cowpox ATI promoters is SEQ ID No: 1 or a polynucleotide which comprises at least 10 nucleotides including nucleotides 22 to 29 of SEQ ID NO:1 and still active as an ATI promoter.

4. Racombinant poxvirus according to claim 1, wherein the Cowpox ATI promoters in each expression cassette, in the recombinant poxvirus are identical to one another.

5. Recombinant poxvirus according to claim 1, wherein at least two expression cassettes are inserted into the same insertion site in the poxvirus genome.

6. Recombinant poxvirus according to claim 1, wherein the Cowpox ATI promoter in at least one of the expression cassettes has the sequence of SEQ ID.: No. 1.

7. Recombinant poxvirus according to claim 1, wherein the Cowpox ATI promoter in the expression cassettes has the sequence of SEQ ID.: No. 1.

8. Recombinant poxvirus according to claim 1, wherein the poxvirus is selected from the group consisting of orthopoxviruses and avipoxviruses.

9. Recombinant poxvirus according to claim 8, wherein the orthopoxvirus is a vaccinia virus and wherein the avipoxvirus is selected from the group consisting of canarypoxvirus and fowlpoxvirus.

10. Recombinant poxvirus according to claim 9, wherein the vaccinia virus is modified vaccinia virus strain Ankara (MVA), in particular MVA-BN and MVA 575, deposited under numbers VO0083008 and V00120707, respctively, at the European Collection of Animal Cell Cultures (ECACC).

11. Recombinant poxvirus according to claim 10, wherein at least one of the expression cassettes is inserted in a naturally occurring deletion site of the MVA genome with respect to the genome of the vaccinia virus strain Copenhagen.

12. Recombinant poxvirus according to claim 1, wherein at least one of the expression cassettes is inserted in an intergenic region of the poxvirus genome.

13. Recombinant poxvirus according to claim 1, wherein at least one of the coding sequences codes for at least one antigen, antigenic epitope, and/or a therapeutic compound.

14. Vaccine or pharmaceutical composition comprising a recombinant poxvirus according to claim 1.

15. Method for introducing coding sequences into target cells comprising the infection of the target cells with the virus according to claim 1.

16. Method for producing a peptide, protein and/or virus comprising:

a) infection of a host cell with the recombinant poxvirus according to claim 1, b) cultivation of the infected host cell under suitable conditions, and c) isolation and/or enrichment of the peptide and/or protein and/or viruses produced by said host cell.

17. Method for effecting an immunological response in a living animal host including a human comprising administering the virus according to claim 1 to the animal or human to be treated.

18. Method according to claim 17 comprising the administration of at least $10^2$ $TCID_{50}$ (tissue culture infectious dose) of the virus.

19. A cell containing the virus according to claim 1.

20. A method for the production of a recombinant virus according to claim 1 comprising the step of inserting at least two expression cassettes into the genome of a poxvirus.

21. Method for effecting an immunological response in a living animal host, including a human, comprising administering the composition or vaccine according to claim 14 to the animal or human to be treated.

* * * * *